(12) United States Patent
Staal et al.

(10) Patent No.: US 12,186,286 B2
(45) Date of Patent: *Jan. 7, 2025

(54) USE OF SENICAPOC FOR TREATMENT OF STROKE

(71) Applicant: Paracelsus Neuroscience II, LLC, Metuchen, NJ (US)

(72) Inventors: Roland Staal, Metuchen, NJ (US); Jonathan Weinstein, Seattle, WA (US); Thomas Moeller, Brookline, MA (US)

(73) Assignee: Paracelsus Neuroscience LLC, Metuchen, NJ (US)

( * ) Notice: Subject to any disclaimer, the term of this patent is extended or adjusted under 35 U.S.C. 154(b) by 193 days.

This patent is subject to a terminal disclaimer.

(21) Appl. No.: 17/813,158

(22) Filed: Jul. 18, 2022

(65) Prior Publication Data

US 2023/0045322 A1     Feb. 9, 2023

Related U.S. Application Data

(63) Continuation of application No. 16/481,779, filed on Jul. 29, 2019, now Pat. No. 11,395,807.

(51) Int. Cl.
| | | |
|---|---|---|
| *A61K 31/165* | (2006.01) | |
| *A61K 9/00* | (2006.01) | |
| *A61P 9/10* | (2006.01) | |

(52) U.S. Cl.
CPC .......... *A61K 31/165* (2013.01); *A61K 9/0019* (2013.01); *A61K 9/0053* (2013.01); *A61P 9/10* (2018.01)

(58) Field of Classification Search
CPC .................................................. A61K 31/165
See application file for complete search history.

(56) References Cited

U.S. PATENT DOCUMENTS

| | | | |
|---|---|---|---|
| 6,288,122 B1 * | 9/2001 | McNaughton-Smith | A61P 7/00 564/181 |
| 11,395,807 B2 * | 7/2022 | Staal | A61K 31/165 |
| 11,439,607 B2 * | 9/2022 | Staal | A61P 29/02 |
| 2005/0000973 A1 | 1/2005 | Stephenson | |
| 2014/0029633 A1 | 10/2014 | Suh | |
| 2016/0033172 A1 | 2/2016 | Crawmer et al. | |
| 2016/0033178 A1 | 2/2016 | Ouellette | |

FOREIGN PATENT DOCUMENTS

WO     2016/134353 A1     8/2016

OTHER PUBLICATIONS

Q. Yang et al., Potential Neuroprotective Treatment of Stroke: Targeting Excitotoxicity, Oxidative Stress, and Inflammation, Front. Neurosci., Sep. 27, 2019, https://doi.org/10.3389/fnins.2019.01036.
Yousufuddin M, Young N. Aging and ischemic stroke. Aging (Albany NY). 2019;11(9):2542-2544. doi:10.18632/aging.101931.
International Preliminary Report on Patentability, dated Apr. 5, 2019.
International Preliminary Report on Patentability, dated Jan. 26, 2019.
Letter in Response to the Written Opinion, dated Jun. 21, 2018.
Written Opinion of the International Searching Authority, dated Apr. 12, 2018.
Handbook of Clinical Neurology, 2012A. Martins Da Silva and L. James Willmore, "Posttraumatic epilepsy" in Handbook of Clinical Neurology, vol. 108 (3rd series), Epilepsy, Part II H. Stefan and W.H. Theodore, Editors, Elsevier 2012 (see highlighted text, p. 591, right col, middle).
Centers for Disease Control, "Types of Stroke," https://www.cdc.gov/stroke/types_of_stroke.htm.

* cited by examiner

*Primary Examiner* — Rei Tsang Shiao
(74) *Attorney, Agent, or Firm* — Andrew H. Berks

(57) ABSTRACT

Neuroinflammation mediated by microglia and infiltrating peripheral immune cells is a major component of stroke pathophysiology. The calcium activated potassium channel $K_{Ca}3.1$ is expressed selectively in the injured CNS by microglia, and $K_{Ca}3.1$ function has been implicated in proinflammatory activation of microglia. $K_{Ca}3.1$ is further implicated in the pathophysiology of ischemia/reperfusion (stroke) related brain injury. Senicapoc, an investigational drug with a proven safety profile and shown to cross the blood-brain barrier, is a potent and selective $K_{Ca}3.1$ inhibitor that intervenes in the inflammation cascade that follows ischemia/reperfusion, and is a potential treatment for stroke.

3 Claims, 4 Drawing Sheets

USE OF SENICAPOC FOR TREATMENT OF STROKE

FIELD OF INVENTION

This invention pertains to the treatment of stroke with senicapoc.

BACKGROUND

Stroke is the leading cause of serious long-term disability and the fifth leading cause of death in the United States (Mozaffarian et al., 2015). Treatment options for stroke are few in number and limited in efficacy (Prabhakaran et al., 2015). The cellular response to acute ischemic stroke, particularly the response of immune cells, has been studied extensively and has been recently reviewed in detail (Iadecola and Anrather, 2011; Macrez et al., 2011). The kinetics of post-stroke immune reactions are critical in post-ischemic physiology and the concept of a biphasic or multi-phasic response to brain ischemia is now favored (Hayakawa et al., 2010; Lo, 2008; Maki et al., 2013). Post-ischemic inflammation is characterized by a sequence of events involving the brain, its vessels, the circulating blood and lymphoid organs. Many of these processes play a central role in preconditioning-mediated neuroprotection (McDonough and Weinstein, 2016).

Microglia are central nervous system (CNS)-resident immune cells (Benarroch, 2013; Michell-Robinson et al., 2015) derived from yolk sac macrophages that enter the CNS during early development and maintain themselves as a distinct population from circulating monocytes (Ginhoux et al., 2010). Microglia contribute to the maintenance of brain homeostasis by pruning synapses, clearing dead or dying cells as well as providing trophic support to other cells (Zuchero and Barres, 2015). These functions suggest that microglia play a critical role in the normal physiology and development of the CNS (Jha et al., 2015). Microglia play a significant role in the neuroinflammatory response to ischemia (Weinstein et al., 2010). The expression of Toll-like receptors (TLRs) and other pattern recognition receptors by microglia enables them to identify pathogens and upregulate a unique profile of effector immune cytokines and chemokines in response to a wide range of stimuli (van Rossum and Hanisch, 2004). Most abundantly expressed by microglia is TLR4, and both endogenous and exogenous TLR4 agonists potently activate classical pro-inflammatory responses in microglia (Dave et al., 2006; van Rossum and Hanisch, 2004).

Although microglial activation has typically been considered a pro-inflammatory process, recent publications suggest that microglia could play a protective role in stroke (Lalancette-Hebert et al., 2007; Nedergaard and Dirnagl, 2005) through multiple mechanisms such as metabolic and physiological support of neurons (van Rossum and Hanisch, 2004), production of trophic factors (Nedergaard and Dirnagl, 2005), autophagy of damaged and repair of lesioned tissue (Cunningham et al., 2005). Microglia are the first responders to ischemic injury, activating before peripheral monocytes/macrophages infiltrate the CNS (Umekawa et al., 2015). Ischemia induces robust increases in microglia cell number (Denes et al., 2007; McDonough and Weinstein, 2016) and proliferation (Denes et al., 2007). Pharmacologic or genetic ablation of microglia influences outcome in multiple rodent models of stroke (Lalancette-Hebert et al., 2007; Szalay et al., 2016). These findings have provided strong evidence to support a key role for innate immune signaling and microglia in both ischemia-induced injury and neuroprotection.

The effects of microglial activation and its role in post-ischemic inflammation is shown schematically in FIG. 1 (Staal et al., Neurochem Res. 2017). As shown in FIG. 1, astrocytes (AS) provide trophic support to neurons (N) through multiple mechanisms and secrete transforming growth factor β (TGFβ), which is reparative to endothelial cells (EC). Both microglia (MG) and astrocytes secrete pro-inflammatory cytokines (tumor necrosis factor α (TNFα), IL-1β, IL-6, IL-17) in response to ischemia. Neurons also signal via fractalkine (CX3CL1) to microglia which express cognate receptor CX3CR1. Both astrocytes and peripheral immune cells (PIC) are potential sources of type 1 inteferons (IFNα, β) that signal to microglia via IFNAR, triggering transcription of interferon stimulated genes (ISGs). ISG protein products may enhance oligodendrocyte (OL) viability in the setting of prolonged ischemia and in turn increase axonal integrity in white matter. The latter may limit long-term ischemia-induced injury to neural networks and protect the white matter-based connectome. ECs and other cells release danger associated molecular patterns (DAMPs), such as fibronectin, high mobility group box 1 (HMGB1), peroxiredoxin (PRX) and heat shock proteins (HSPs) that are endogenous ligands for numerous TLRs. PICs are capable of secreting many different cytokines, which have effects on multiple cell types.

Thus, pharmaco-therapeutics that can specifically modulate microglial gene expression and phenotype in the context of ischemia may be able to effectively skew the neuroimmune response in a direction that is more favorable to both neuronal survival and axonal/white matter integrity.

The calcium activated potassium channel $K_{Ca}3.1$ is constitutively expressed in the CNS by cerebrovascular cells. It is also expressed by microglia following injury to the CNS (Chen et al., 2015). $K_{Ca}3.1$ leads to potassium efflux thereby increasing the driving force for $Ca^{2+}$ entry, and subsequently affecting $Ca^{2+}$ dependent immune mechanisms. It has been shown that microglia in vitro express $K_{Ca}3.1$ and that its inhibition reduces production and release of nitric oxide (NO) and interleukin 1β (IL-1β) from appropriately stimulated microglia (Dale et al., 2016) (FIG. 1). Other studies have shown that inhibition of $K_{Ca}3.1$ reduces microglial synthesis of enzymes involved in production of eicosanoids (COX-2) and nitric oxide (iNOS) (Nguyen et al., 2016). Accordingly, inhibition of $K_{Ca}3.1$ is expected to have a broad range of anti-inflammatory effects.

Several inhibitors of $K_{Ca}3.1$ have been reported (Wulff and Castle, 2010; Wulff et al., 2007). However, early inhibitors lacked potency and selectivity and were hampered by safety concerns (Suzuki et al., 2000; Wulff and Castle, 2010; Zhang et al., 2002).

TRAM-34 was described as a selective inhibitor of $K_{Ca}3.1$ with good potency and good CNS penetration. TRAM-34 potently inhibits $K_{Ca}3.1$ channels with an $IC_{50}$ of 20 nM in recombinant cell lines and has no effect on cytochrome P450-dependent enzymes (Wulff et al., 2000). It has been used to investigate the physiology of $K_{Ca}3.1$ channels in immune cells and the involvement of $K_{Ca}3.1$ channels in several CNS disorders, including multiple sclerosis (Reich et al., 2005), optic nerve transection (Kaushal et al., 2007), spinal cord injury (Bouhy et al., 2011), ischemic stroke (Chen et al., 2011; Chen et al., 2015), and glioblastoma multiforme (D'Alessandro et al., 2013). Wulff and colleagues evaluated TRAM-34 in a rat model of ischemic stroke (Chen et al., 2011). After administration of TRAM-34 at 40 mg/kg intraperitoneal (i.p.), plasma and brain concentrations reached ~1 µmol/L at 8 hours, dropping to 0.4 µmol/L by 12 hours. Free plasma concentrations were determined to be approximately 2%. From these data, it is estimated that the plasma and brain concentrations are 20 nM and 8 nM, respectively, at 12 hours (before the second dose). Thus, when given i.p. the TRAM-34 concentrations are at or near the $IC_{50}$ values for $K_{Ca}3.1$ inhibition. The high doses needed to achieve concentrations above $IC_{50}$ values, however, suggested that bioavailability for TRAM-34 is a significant issue.

Unbound CNS levels of the TRAM-34 are not much higher than the $IC_{50}$ for $K_{Ca}3.1$ inhibition in microglia in vitro and the $t_{1/2}$ suggests that CNS $K_{Ca}3.1$ inhibition is only achieved for a few hours after administration. While it is always challenging to develop a CNS penetrant drug able to provide 24-hour coverage even with a multiple dosing paradigm, there is significant room for improvement in drug levels achieved as well as $t_{1/2}$. Modulating the neuroimmune response, and the microglial/macrophage phenotype in particular, is an attractive target in acute ischemic stroke therapy in part because this response evolves gradually over days to weeks, whereas many previously targeted physiological phenomena in stroke, such as glutamate-dependent excitotoxicity for example, tend to occur rapidly (minutes to hours after stroke onset) (Dirnagl, 2012). Thus, targeting the neuroimmune response in stroke offers a broader temporal therapeutic window and could translate to therapies beyond the current three to six-hour time window. Administration of TRAM-34 at both 10 and 40 mg/kg i.p. significantly attenuated post stroke infarct volume and neuronal loss. TRAM-34 also improved the neurological deficit score and significantly reduced the extent of microglial ED1 staining. Especially promising was the finding that TRAM-34 improved the outcome in this model of stroke even when given 12 hours after the ischemic insult. Current pharmacologic treatments for acute ischemic stroke need to be given within 3-4.5 hours (Prabhakaran et al., 2015), a temporal challenge that severely limits the reach of currently available therapies.

While TRAM-34 showed selectivity for $K_{Ca}3.1$ over other calcium-activated potassium channels (Wulff et al., 2000), it might have inhibited additional targets, confounding the interpretation of any results (Schilling and Eder, 2007). Schilling and Eder have demonstrated that TRAM-34 blocks non-selective cation current in primary microglia stimulated with lysophosphatidylcholine (LPC) with an $IC_{50}$ that was similar to its $IC_{50}$ for $K_{Ca}3.1$ channels (Schilling and Eder, 2007). Furthermore, another presumed $K_{Ca}3.1$ blocker, charybdotoxin, had no effect on LPC signals (Schilling and Eder, 2007). Hence, TRAM-34 may modulate immune cell function by a mechanism unrelated to $K_{Ca}3.1$ inhibition. Furthermore, it has recently been demonstrated that TRAM-34 still inhibits some cytochrome P450 isoforms, namely human CYP2B6, CYP2C19 and CYP3A4 with $IC_{50}$ values in the low micromolar range (Agarwal et al., 2013).

In addition, TRAM-34 shows metabolic instability and has a short half-life (~2 hours in rats and primates) potentially complicating chronic dosing (Maezawa et al., 2012). Thus, although TRAM-34 is a valuable experimental and potentially effective therapeutic agent, it has issues that may confound interpretation of mechanism in preclinical models and may limit its clinical utility.

Another reported $K_{Ca}3.1$ inhibitor is NS6180, (4-[[3-(trifluoromethyl)phenyl]methyl]-2H-1,4-benzothiazin-3(4H)-one) (Strøbæk, et al., 2013). NS6180 was reported to have similar potency and selectivity to TRAM-34.

An alternative $K_{Ca}3.1$ inhibitor is senicapoc (ICA-17043), a potent, CNS penetrant inhibitor with improved stability and selectivity vs TRAM-34 (Dale et al., 2016; Strøbæk, et al., 2013; Schilling and Eder, 2007). Senicapoc is an experimental drug described in U.S. Pat. No. 6,288,122. Senicapoc has previously been investigated for the treatment of sickle cell anemia (Ataga et al. 2008) and malaria (Tubman et al. 2016). However, a phase III clinical trial for sickle cell disease found that despite improvements in hematological parameters, there was no improvement in sickle cell painful crises observed, so development activities were halted (Ataga et al., 2011). Significantly, the sickle cell clinical trial was not terminated for safety or toxicity reasons.

SUMMARY OF THE INVENTION

In view of the demonstrated selective inhibition of on $K_{Ca}3.1$ by senicapoc, concurrent reduction of nitric oxide and regulation on $Ca^{++}$ signaling, and the ability of senicapoc to cross the blood-brain barrier, senicapoc exerts a neuroprotective effect and can prevent or reduce stroke or ischemic-induced injury in a patient at risk for stroke or ischemic-induced injury, or in acute ischemic stroke patients. Moreover, because of the anti-inflammatory effect of inhibition of $K_{Ca}3.1$, senicapoc is useful for treating a patient suffering from stroke or ischemic injury and reducing the neuroinflammation associated with these conditions.

Accordingly, in an embodiment, a method is provided of preventing or treating stroke by the administration of senicapoc to a patient at immediate risk for stroke or ischemic-induced injury or who is actively suffering from acute stroke or ischemia-induced injury. In an embodiment, senicapoc is used in the manufacture of a medicament for the prevention or treatment of stroke by the administration of senicapoc to a patient at risk for stroke or ischemic-induced injury or suffering from stroke or ischemic-induced injury. In an embodiment, an oral dosage form of senicapoc is provided for use in preventing or treating stroke by the administration of senicapoc to a patient at risk for stroke or ischemic-induced injury or suffering from stroke or ischemia-induced injury.

with an $EC_{50}$ of 0.9 nM as shown in a representative experiment (n=3). (B) Primary rat cortical microglia were incubated with LPS (3 EU/ml) for 24 hours to induce expression of IL-1β. Senicapoc dose dependently inhibited IL-1β release from primary microglia with an $IC_{50}$ of 1.3 nM (n=3).

DETAILED DESCRIPTION

Stroke is the leading cause of serious long-term disability and the fifth leading cause of death in the United States. Treatment options for stroke are limited and have limited efficacy. Neuroinflammation mediated by microglia and infiltrating peripheral immune cells is a major component of stroke pathophysiology. Interfering with the inflammation cascade after stroke holds the promise to modulate stroke outcome. The calcium activated potassium channel $K_{Ca}3.1$ is expressed selectively in the injured CNS by microglia. $K_{Ca}3.1$ function has been implicated in pro-inflammatory activation of microglia and there is recent literature suggesting that this channel is important in the pathophysiology of ischemia/reperfusion (stroke) related brain injury. Accordingly, senicapoc, a $K_{Ca}3.1$ inhibitor, may intervene in the inflammation cascade that follows ischemia/reperfusion and limit the damage caused by stroke or other ischemic injury.

Figure 1:
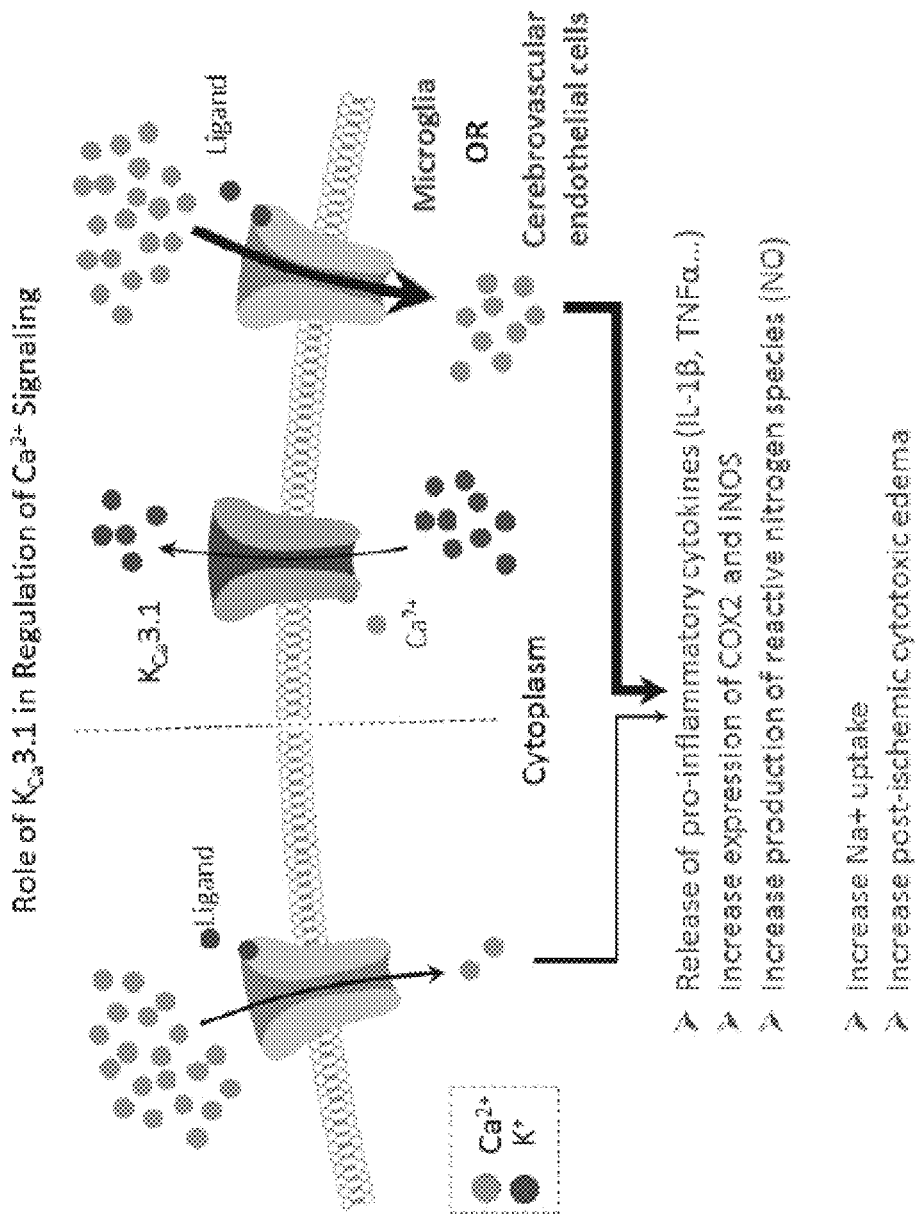
FIG. 1 is a schematic showing key neuroimmune pathways and interactions between cells of the CNS in ischemic inflammation and the points of senicapoc activity.
Figure 2:
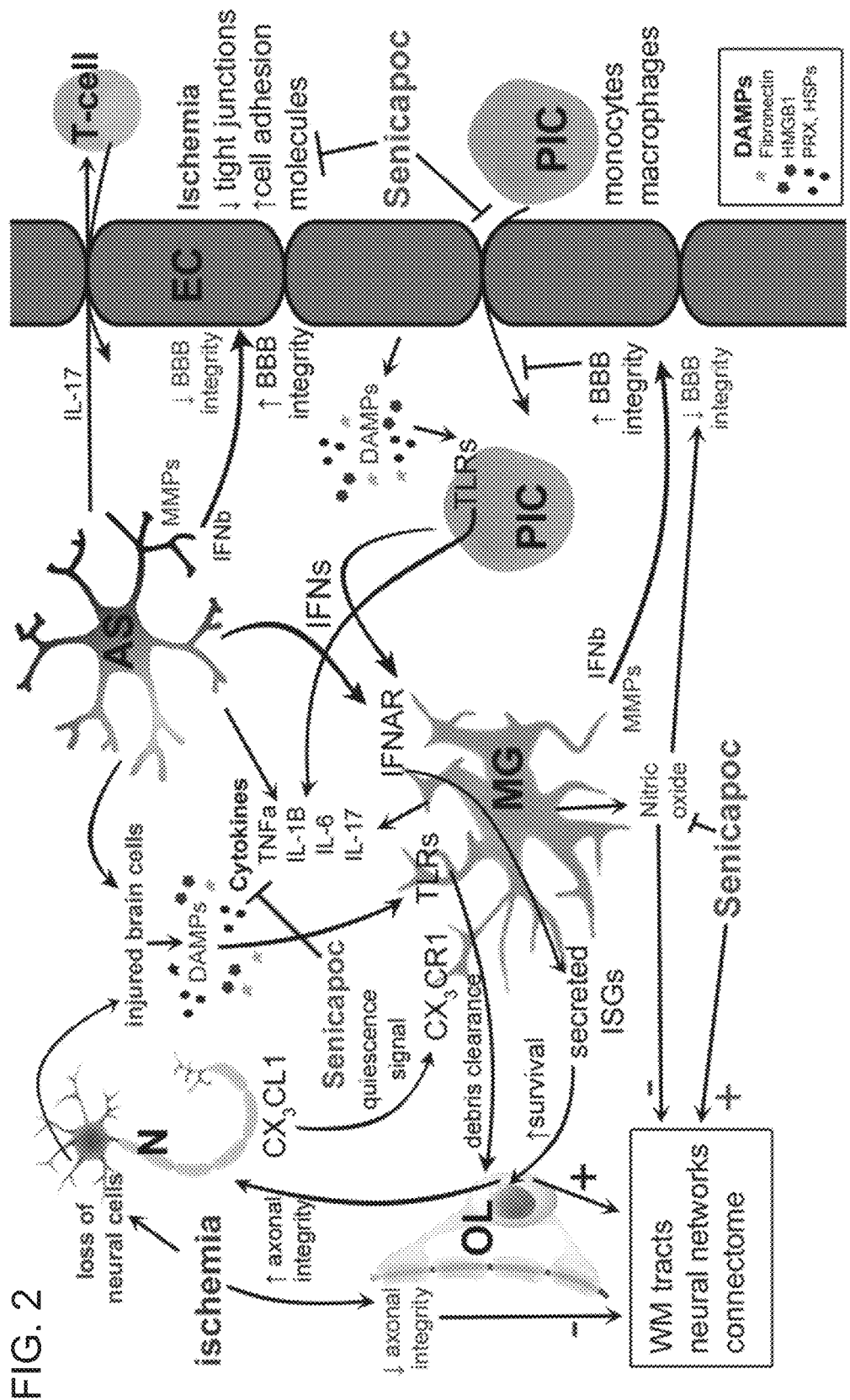
FIG. 2. Effect of $K_{Ca}3.1$ inhibition on NO and regulation of $Ca^{++}$ signaling. All downstream effects in microglia (shown in green) and cerebrovascular endothelial cells (shown in red) are attenuated by senicapoc electrophysiology.

Senicapoc attenuates pro-inflammatory responses in microglia (reducing release of cytokines and nitric oxide) and in epithelial cells attenuating ischemia-induced disruption of the blood-brain barrier (BBB) (FIG. 1) (Staal et al., Neurochem Res. 2017). By modulating elements of the microglial and epithelial cells response to ischemia, senicapoc may influence the neural environment indirectly in a number of ways, for example by enhancing white matter integrity as shown in FIG. 1.

The ability of senicapoc to inhibit the potassium channel $K_{Ca}3.1$ is discussed in detail in our co-pending patent application PCT/US17/57930, filed Oct. 23, 2017.

Figure 3A:
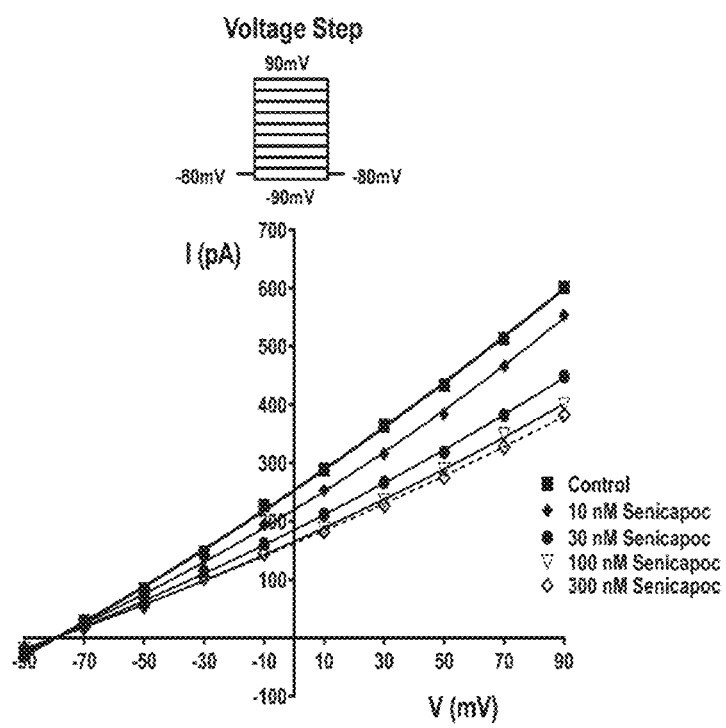
FIG. 3A and FIG. 3B. $K_{Ca}3.1$ electrophysiology in rat microglial cells exposed to control or senicapoc. $K^+$ currents were recorded from primary microglia by using either (A) depolarizing steps or (B) a voltage ramp protocol. In both paradigms, the currents reversed at 0 mV which was the equilibrium potential for $K^+$. Senicapoc dose dependently inhibited a significant part of the $K^+$ current.
Figure 3B:
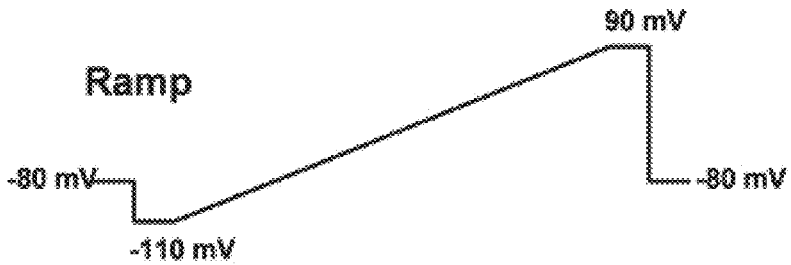
Figure 3B:
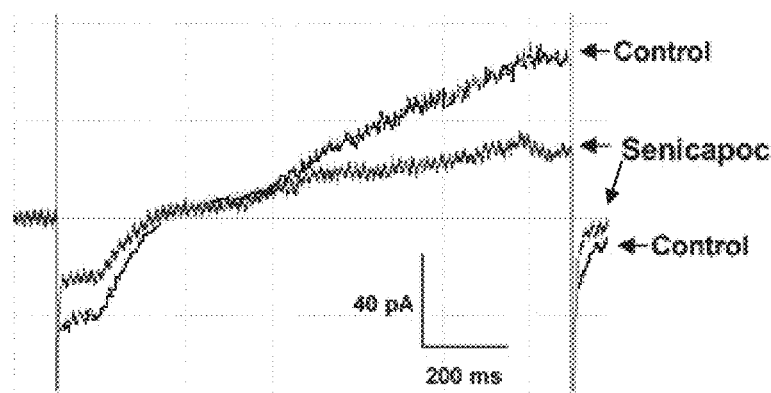

$K_{Ca}3.1$ is highly expressed on microglia in vitro (Kaushal et al., 2007). The effect of senicapoc was evaluated on microglial $K^+$ currents elicited by either depolarizing steps (FIG. 3A) or a voltage ramp protocol (FIG. 3B) using automated patch clamp analysis. Senicapoc dose dependently (10, 100, 300 and 1000 nM) inhibited the microglial $K^+$ current although not completely (FIG. 3A) with an $IC_{50}$ of 10 nM. This value is in close agreement with the $IC_{50}$ value (10 nM) generated by patch-clamp studies on CHO-$K_{Ca}3.1$ cells. Some residual $K^+$ current still remained which was most likely not $K_{Ca}3.1$-sensitive (Kettenmann et al., 2011).

Figure 4A:
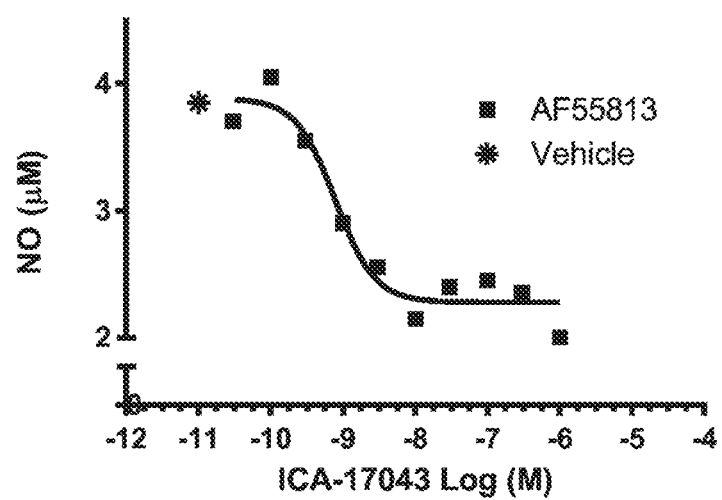
FIG. 4A and FIG. 4B. Effect of $K_{Ca}3.1$ inhibition on NO and IL-1β release from primary microglia. (A) Primary rat cortical microglia were pre-treated with vehicle or senicapoc at concentrations indicated for 30 minutes followed by addition of lipopolysaccharide (LPS) (3 EU/ml) and incubated for a total of 24 hours. Senicapoc inhibited the production of NO (as measured by its metabolite, nitrite)
Figure 4B:
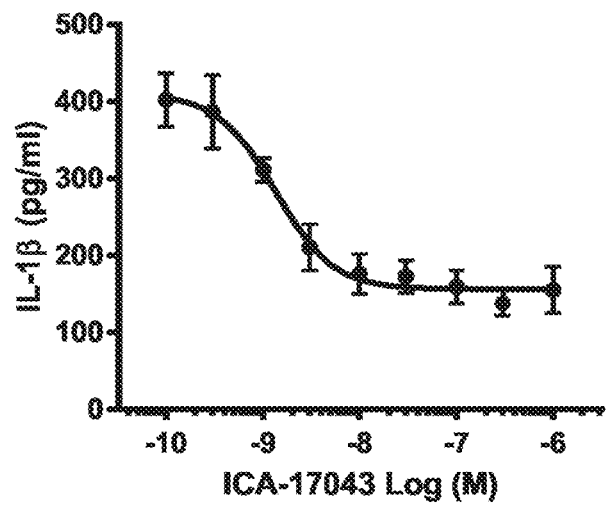

To show the inhibition of nitric oxide and IL-1β, primary rat cortical microglia were incubated with either vehicle or senicapoc for 30 minutes prior to the addition of vehicle or ultrapure LPS (3 EU/ml) to stimulate iNOS expression and NO release. After 24 hours, media was assayed for nitrite (stable metabolite of NO). Senicapoc dose dependently inhibited the release of NO from LPS-treated microglia with an average $IC_{50}$ of 39 nM (FIG. 4A), in agreement with previous studies (Kaushal et al., 2007; Khanna et al., 2001). Primary rat cortical microglia were also treated with LPS (3 EU/ml, 3 hours) to stimulate the production of pro-IL-1β. Next, vehicle or senicapoc were added and incubated for an additional 30 minutes followed by the addition of BzATP (1 mM) to activate P2X7 receptors and trigger the activation of caspase 1, its cleavage pro-IL-1β and the release of the liberated IL-1β (another 30 minutes). Senicapoc dose dependently inhibited IL-1β release from primary microglia with an $IC_{50}$ of 15 nM (FIG. 4B).

Unlike TRAM-34, senicapoc has no known off target effects at concentrations that block $K_{Ca}3.1$ (Staal et al., 2017). It also does not suffer from metabolic instability or effects on cytochrome P450. Most importantly, senicapoc has been tested in humans in clinical trials without any significant side effects. The finding that senicapoc is also CNS penetrant opens up its use for CNS indications.

While many devastating neurological and perhaps psychiatric diseases could be potentially treated by senicapoc, the studies of selective inhibitor of $K_{Ca}3.1$ with high potency and good CNS penetration as a treatment for stroke lay a foundation for the use of senicapoc on stroke patients.

Finding a treatment for stroke that can be given beyond the narrow therapeutic window of current treatments would be a major advance. The data on efficacy of the $K_{Ca}3.1$ inhibitor, TRAM-34, outside of this narrow therapeutic window suggests that inhibition of $K_{Ca}3.1$ could become a promising treatment strategy in acute stroke. The potent and selective $K_{Ca}3.1$ inhibitor senicapoc ($IC_{50}$ of 11 nM) was initially developed for the treatment of sickle cell anemia (Ataga et al., 2006; Ataga et al., 2011; Ataga et al., 2008; Ataga and Stocker, 2009). The drug was well tolerated in Phase 1 clinical trials in both healthy volunteers and in patients with sickle cell disease (Ataga et al., 2006; Ataga et al., 2011). In a double-blind placebo controlled Phase 2 study, senicapoc (at 10 mg/day) reduced hemolysis and significantly increased hematocrit and hemoglobin levels in patients with sickle cell disease (Ataga et al., 2008). In a subsequent Phase 3 trial, senicapoc was tested for its effects on vaso-occlusive pain crisis (Ataga et al., 2011). However, despite properly engaging erythrocyte $K_{Ca}3.1$, reducing hemolysis and increasing hemoglobin and hematocrit levels, senicapoc had no effect on pain outcome measures and the trial was terminated (Ataga et al., 2011). While this was disappointing, it is important to point out that the drug did what it was supposed to do on a molecular and cellular level. The clinical trial failed because the outcome measure chosen were distal to the proposed mode of action and perhaps not completely dependent on this mechanism.

Importantly, senicapoc has been shown to cross the blood-brain barrier. While the peripheral pharmacokinetics of senicapoc have been described in detail (McNaughton-Smith et al., 2008), the ability of senicapoc to cross the blood-brain barrier has only recently been reported (Staal et al., 2017). After 10 mg/kg oral dosing in rats, senicapoc achieved free plasma concentrations of 17 and 65 nM and free brain concentrations of 37 and 136 nM at one and four hours post-dose, respectively. Cerebrospinal fluid (CSF) concentrations were determined to be 25 and 121 nM at one and four hours post-dosing which are in-line with the free brain concentrations. These data suggest that senicapoc achieves CNS concentrations greater than its $IC_{50}$ value for $K_{Ca}3.1$ channels (11 nM) and thus should be sufficient to inhibit it (McNaughton-Smith et al., 2008). Furthermore, senicapoc achieves free brain concentrations several fold higher than TRAM-34.

In the same study, senicapoc's selectivity was assessed in a screen of ~70 additional neuronal drug targets (50 neuronal receptors, 8 enzymes, 5 transporters and 7 ion channels) (Staal et al., 2017). None of the targets tested was inhibited by senicapoc at 1 μM, providing additional evidence that senicapoc is selective for $K_{Ca}3.1$ channels. In vivo, senicapoc was tested in the chronic constriction injury model of neuropathic pain (Bennett and Xie, 1988). Senicapoc dose dependently (10, 30 and 100 mg/kg p.o.) attenuated the mechanical hypersensitivity induced by the peripheral nerve injury, although only the highest dose was significant (Staal et al., 2017). Furthermore, in contrast to reported locomotor effects in kcnn4$^{-/-}$ mice (Lambertsen et al., 2012) that have no functional $K_{Ca}$3.1, the authors did not observe any significant impact of senicapoc on locomotor activity (Staal et al., 2017). While the study does not shed light on the cell types in the CNS that express $K_{Ca}$3.1, it clearly demonstrates that senicapoc was efficacious in ameliorating pain behaviors in rats with peripheral nerve injury and these conclusions were supported by the free drug concentrations attained in plasma, brain and CSF.

Numerous active cellular processes and complex cellular interactions contribute to the resolution of post-ischemic inflammation. senicapoc ameliorated pain behaviors in a model of neuropathic pain (Staal et al., 2017). Since experimental surgery-related inflammation is resolved seven days after the animals are tested, it supported the hypothesis that the efficacy was mediated by inhibition of $K_{Ca}$3.1 on microglia in the spinal cord or brain rather than peripheral immune cells. In addition to the prior studies in rats, we report here the ability of senicapoc to penetrate the CNS in mice (see Table 1). The data were similar to those in rats with senicapoc reaching higher levels in brain than plasma and showing a similar $t_{1/2}$ demonstrating that senicapoc readily crossed the blood brain barrier and achieved concentrations well above the $IC_{50}$. Based on the rat and mouse pharmacokinetic data CNS penetrance in humans seems promising.

To address in vivo side effects of senicapoc, the most relevant being sedation in pain models, the effect of the drug on rat locomotor activity was tested (Staal et al., 2017). The results showed that senicapoc did not alter activity at doses required for efficacy in the chronic constriction injury model of neuropathic pain. The data suggests that $K_{Ca}$3.1 inhibition has few adverse effects. The significance of these preclinical findings is enhanced by the human clinical trials that demonstrated that senicapoc is safe and has a low incidence of side effects.

Based on the animal studies, the major drawback to both TRAM-34 and senicapoc is the short half-life (see Table 1). In contrast to the preclinical studies in rodents, clinical trials showed an unexpected $t_{1/2}$ of 23 days in humans. This raises the question whether senicapoc covalently binds to plasma proteins whose $t_{1/2}$ is approximately 21 days which is significantly longer than that of the unbound drug. It is important to note that the potential covalent protein binding, should not impact the ability of senicapoc to penetrate the CNS, although it would make dose titration more complex.

To date, the only CNS disease model in which senicapoc has been evaluated is the chronic constriction injury model of neuropathic pain (Staal et al., 2017).

TABLE 1

Pharmacokinetics of TRAM-34, NS6180 and senicapoc *$IC_{50}$ reported are for human KCa3.1 expressed in recombinant cells. All data are for compounds dosed p.o.

|  |  | TRAM-34 | NS1680 | Senicapoc | Senicapoc |
|---|---|---|---|---|---|
| Molecular Weight (g/mol) |  | 345 | 323 | 323 |  |
| Species |  |  | Rat |  | Mouse |
| Dose (mg/kg) |  | 10 | 10 | 10 | 10 |
| T½ (hours) |  | ~2 | 3.8 | 1 | 3.1 |
| $T_{max}$ (hours) |  | 0.5-1 |  | 4 | 0.33 |
| In-vitro $IC_{50}$ (nM)* |  |  | 20 (Wulff et al 2000) | 9.4 hu | 12 hu |
| $C_{max}$-Total (nM) | Plasma | ~2500 | 186 | 2,400 (Staal et al., 2017) | 709 |
|  | Brain | ~2500 |  | 17,000 (Staal et al., 2017) |  |
| % unbound | Plasma | 2 |  | 2.7 (Staal et al., 2017) | 1.5 |
| $C_{max}$- (nM) | Brain |  |  | 0.8 (Staal et al, 2017) | 0.8 |
| Unbound $C_{max}$- Unbound (nM) | Plasma | 50 |  | 65 |  |
|  | Brain | 50 |  | 136 |  |
|  | CSF |  |  | 121 |  |
| Reference |  | Chen et al., 2011 JCBM | Strøbæk et al, 2013 | McNaughton-Smith, 2008 | Previously unpublished data | hu: tested in vitro in the human receptor.

Compounds and Formulations

In an embodiment, senicapoc may be formulated as an oral pharmaceutical formulation product for use in the prevention or treatment of stroke or ischemic injury as provided herein.

Oral dosage forms include tablets, capsules, and powders for dissolution or suspension in a drink. Such tablets and capsules may be formulated by any of various methods known in the art and may include at least one excipient.

Senicapoc has previously been developed exclusively as an oral formulation, but for stroke patients, an intravenous formulation may be desirable.

REFERENCES

Agarwal, J. J., Zhu, Y., Zhang, Q. Y., Mongin, A. A., Hough, L. B., 2013. TRAM-34, a putatively selective blocker of intermediate-conductance, calcium-activated potassium channels, inhibits cytochrome P450 activity. PLoS One 8, e63028.

Ataga, K. I., Orringer, E. P., Styles, L., Vichinsky, E. P., Swerdlow, P., Davis, G. A., Desimone, P. A., Stocker, J.

W., 2006. Dose-escalation study of ICA-17043 in patients with sickle cell disease. Pharmacotherapy 26, 1557-1564.

Ataga, K. I., Reid, M., Ballas, S. K., Yasin, Z., Bigelow, C., James, L. S., Smith, W. R., Galacteros, F., Kutlar, A., Hull, J. H., Stocker, J. W., Investigators, I.C.A.S., 2011. Improvements in haemolysis and indicators of erythrocyte survival do not correlate with acute vaso-occlusive crises in patients with sickle cell disease: a phase III randomized, placebo-controlled, double-blind study of the Gardos channel blocker Senicapoc (ICA-17043). Br J Haematol 153, 92-104. DOI: 10.1111/j.1365-2141.2010.08520.x Ataga, K. I., Smith, W. R., De Castro, L. M., Swerdlow, P., Saunthararajah, Y., Castro, O., Vichinsky, E., Kutlar, A., Orringer, E. P., Rigdon, G. C., Stocker, J. W., Investigators, I. C. A., 2008. Efficacy and safety of the Gardos channel blocker, Senicapoc (ICA-17043), in patients with sickle cell anemia. Blood 111, 3991-3997.

Ataga, K. I., Stocker, J., 2009. Senicapoc (ICA-17043): a potential therapy for the prevention and treatment of hemolysis-associated complications in sickle cell anemia. Expert Opin Investig Drugs 18, 231-239.

Benarroch, E. E., 2013. Microglia: Multiple roles in surveillance, circuit shaping, and response to injury. Neurology 81, 1079-1088.

Bennett, G. J., Xie, Y. K., 1988. A peripheral mononeuropathy in rat that produces disorders of pain sensation like those seen in man. Pain 33, 87-107.

Bouhy, D., Ghasemlou, N., Lively, S., Redensek, A., Rathore, K. I., Schlichter, L. C., David, S., 2011. Inhibition of the Ca(2)(+)-dependent K(+) channel, KCNN4/KCa3.1, improves tissue protection and locomotor recovery after spinal cord injury. J Neurosci 31, 16298-16308.

Chen, Y. J., Raman, G., Bodendiek, S., O'Donnell, M. E., Wulff, H., 2011. The KCa3.1 blocker TRAM-34 reduces infarction and neurological deficit in a rat model of ischemia/reperfusion stroke. J Cereb Blood Flow Metab 31, 2363-2374.

Chen, Y. J., Wallace, B. K., Yuen, N., Jenkins, D. P., Wulff, H., O'Donnell, M. E., 2015. Blood-brain barrier KCa3.1 channels: evidence for a role in brain Na uptake and edema in ischemic stroke. Stroke 46, 237-244. DOI: 10.1161/STROKEAHA.114.007445

Cunningham, L. A., Wetzel, M., Rosenberg, G. A., 2005. Multiple roles for MMPs and TIMPs in cerebral ischemia. Glia 50, 329-339.

D'Alessandro, G., Catalano, M., Sciaccaluga, M., Chece, G., Cipriani, R., Rosito, M., Grimaldi, A., Lauro, C., Cantore, G., Santoro, A., Fioretti, B., Franciolini, F., Wulff, H., Limatola, C., 2013. KCa3.1 channels are involved in the infiltrative behavior of glioblastoma in vivo. Cell Death Dis 4, e773.

Dale, E., Staal, R. G., Eder, C., Moller, T., 2016. KCa 3.1—a microglial target ready for drug repurposing? Glia 64, 1733-1741.

Dave, K. R., Saul, I., Prado, R., Busto, R., Perez-Pinzon, M. A., 2006. Remote organ ischemic preconditioning protect brain from ischemic damage following asphyxial cardiac arrest. Neurosci Lett 404, 170-175.

Denes, A., Vidyasagar, R., Feng, J., Narvainen, J., McColl, B. W., Kauppinen, R. A., Allan, S. M., 2007. Proliferating resident microglia after focal cerebral ischaemia in mice. J Cereb Blood Flow Metab 27, 1941-1953.

Dirnagl, U., 2012. Pathobiology of injury after stroke: the neurovascular unit and beyond. Ann N Y Acad Sci 1268, 21-25.

Ginhoux, F., Greter, M., Leboeuf, M., Nandi, S., See, P., Gokhan, S., Mehler, M. F., Conway, S. J., Ng, L. G., Stanley, E. R., Samokhvalov, I. M., Merad, M., 2010. Fate mapping analysis reveals that adult microglia derive from primitive macrophages. Science 330, 841-845.

Hayakawa, K., Nakano, T., Irie, K., Higuchi, S., Fujioka, M., Orito, K., Iwasaki, K., Jin, G., Lo, E. H., Mishima, K., Fujiwara, M., 2010. Inhibition of reactive astrocytes with fluorocitrate retards neurovascular remodeling and recovery after focal cerebral ischemia in mice. J Cereb Blood Flow Metab 30, 871-882.

Iadecola, C., Anrather, J., 2011. The immunology of stroke: from mechanisms to translation. Nat Med 17, 796-808.

Jha, M. K., Lee, W. H., Suk, K., 2015. Functional polarization of neuroglia: Implications in neuroinflammation and neurological disorders. Biochem Pharmacol.

Kaushal, V., Koeberle, P. D., Wang, Y., Schlichter, L. C., 2007. The Ca2+-activated K+ channel KCNN4/KCa3.1 contributes to microglia activation and nitric oxide-dependent neurodegeneration. J Neurosci 27, 234-244.

Lalancette-Hebert, M., Gowing, G., Simard, A., Weng, Y. C., Kriz, J., 2007. Selective ablation of proliferating microglial cells exacerbates ischemic injury in the brain. J Neurosci 27, 2596-2605.

Lambertsen, K. L., Gramsbergen, J. B., Sivasaravanaparan, M., Ditzel, N., Sevelsted-Moller, L. M., Olivan-Viguera, A., Rabjerg, M., Wulff, H., Kohler, R., 2012. Genetic KCa3.1-deficiency produces locomotor hyperactivity and alterations in cerebral monoamine levels. PLoS One 7, e47744.

Lo, E. H., 2008. A new penumbra: transitioning from injury into repair after stroke. Nat Med 14, 497-500.

Macrez, R., Ali, C., Toutirais, O., Le Mauff, B., Defer, G., Dirnagl, U., Vivien, D., 2011. Stroke and the immune system: from pathophysiology to new therapeutic strategies. Lancet Neurol 10, 471-480.

Maezawa, I., Jenkins, D. P., Jin, B. E., Wulff, H., 2012. Microglial KCa3.1 Channels as a Potential Therapeutic Target for Alzheimer's Disease. Int J Alzheimers Dis 2012, 868972.

Maki, T., Hayakawa, K., Pham, L. D., Xing, C., Lo, E. H., Arai, K., 2013. Biphasic mechanisms of neurovascular unit injury and protection in CNS diseases. CNS Neurol Disord Drug Targets 12, 302-315.

McDonough, A., Weinstein, J. R., 2016. Neuroimmune Response in Ischemic Preconditioning. Neurotherapeutics 13, 748-761.

McNaughton-Smith, G. A., Burns, J. F., Stocker, J. W., Rigdon, G. C., Creech, C., Arrington, S., Shelton, T., de Franceschi, L., 2008. Novel inhibitors of the Gardos channel for the treatment of sickle cell disease. J Med Chem 51, 976-982.

Michell-Robinson, M. A., Touil, H., Healy, L. M., Owen, D. R., Durafourt, B. A., Bar-Or, A., Antel, J. P., Moore, C. S., 2015. Roles of microglia in brain development, tissue maintenance and repair. Brain 138, 1138-1159.

Mozaffarian, D., Benjamin, E. J., Go, A. S., Arnett, D. K., Blaha, M. J., Cushman, M., de Ferranti, S., Despres, J. P., Fullerton, H. J., Howard, V. J., Huffman, M. D., Judd, S. E., Kissela, B. M., Lackland, D. T., Lichtman, J. H., Lisabeth, L. D., Liu, S., Mackey, R. H., Matchar, D. B., McGuire, D. K., Mohler, E. R., 3rd, Moy, C. S., Muntner, P., Mussolino, M. E., Nasir, K., Neumar, R. W., Nichol, G., Palaniappan, L., Pandey, D. K., Reeves, M. J., Rodriguez, C. J., Sorlie, P. D., Stein, J., Towfighi, A., Turan, T. N., Virani, S. S., Willey, J. Z., Woo, D., Yeh, R. W., Turner, M. B., American Heart Association Statistics, C., Stroke Statistics, S., 2015. Heart disease and stroke statistics—2015 update: a report from the American Heart Association. Circulation 131, e29-322.

Nedergaard, M., Dirnagl, U., 2005. Role of glial cells in cerebral ischemia. Glia 50, 281-286.

Nguyen, H. M., Grossinger, E. M., Horiuchi, M., Davis, K. W., Jin, L. W., Maezawa, I., Wulff, H., 2016. Differential Kv1.3, KCa3.1, and Kir2.1 expression in "classically" and "alternatively" activated microglia. Glia.

Prabhakaran, S., Ruff, I., Bernstein, R. A., 2015. Acute stroke intervention: a systematic review. JAMA 313, 1451-1462.

Reich, E. P., Cui, L., Yang, L., Pugliese-Sivo, C., Golovko, A., Petro, M., Vassileva, G., Chu, I., Nomeir, A. A., Zhang, L. K., Liang, X., Kozlowski, J. A., Narula, S. K., Zavodny, P. J., Chou, C. C., 2005. Blocking ion channel KCNN4 alleviates the symptoms of experimental autoimmune encephalomyelitis in mice. Eur J Immunol 35, 1027-1036.

Schilling, T., Eder, C., 2007. TRAM-34 inhibits nonselective cation channels. Pflugers Arch 454, 559-563.

Staal, R. G., Khayrullina, T., Zhang, H., Davis, S., Fallon, S. M., Cajina, M., Nattini, M. E., Hu, A., Zhou, H., Poda, S. B., Zorn, S., Chandrasena, G., Dale, E., Cambpell, B., Biilmann Ronn, L. C., Munro, G., Miler, T., 2017. Inhibition of the potassium channel KCa3.1 by senicapoc reverses tactile allodynia in rats with peripheral nerve injury. Eur J Pharmacol 795, 1-7.

Staal, R. G. W., Weinstein, J. R., Nattini, M. et al. Senicapoc: Repurposing a Drug to Target Microglia $K_{Ca}3.1$ in Stroke. Neurochem Res (2017) 42: 2639. DOI: 10.1007/s11064-017-2223-y Strøbæk, D., Brown, D., Jenkins, D., Chen, Y.-J., Coleman, N., Ando, Y., Chiu, P., Jorgensen, S., Demnitz, J., Wulff, H. and Christophersen, P. (2013), NS6180, a new KCa3.1 channel inhibitor prevents T-cell activation and inflammation in a rat model of inflammatory bowel disease. Br J Pharmacol, 168: 432-444. doi:10.1111/j.1476-5381.2012.02143.x Suzuki, S., Kurata, N., Nishimura, Y., Yasuhara, H., Satoh, T., 2000. Effects of imidazole antimycotics on the liver microsomal cytochrome P450 isoforms in rats: comparison of in vitro and ex vivo studies. Eur J Drug Metab Pharmacokinet 25, 121-126.

Szalay, G., Martinecz, B., Lenart, N., Kornyei, Z., Orsolits, B., Judak, L., Csaszar, E., Fekete, R., West, B. L., Katona, G., Rozsa, B., Denes, A., 2016. Microglia protect against brain injury and their selective elimination dysregulates neuronal network activity after stroke. Nat Commun 7, 11499.

Umekawa, T., Osman, A. M., Han, W., Ikeda, T., Blomgren, K., 2015. Resident microglia, rather than blood-derived macrophages, contribute to the earlier and more pronounced inflammatory reaction in the immature compared with the adult hippocampus after hypoxia-ischemia. Glia 63, 2220-2230.

van Rossum, D., Hanisch, U. K., 2004. Microglia. Metab Brain Dis 19, 393-411.

Weinstein, J. R., Koerner, I. P., Moller, T., 2010. Microglia in ischemic brain injury. Future Neurol 5, 227-246. DOI: 10.2217/fnl.10.1

Wulff, H., Castle, N. A., 2010. Therapeutic potential of KCa3.1 blockers: recent advances and promising trends. Expert Rev Clin Pharmacol 3, 385-396.

Wulff, H., Kolski-Andreaco, A., Sankaranarayanan, A., Sabatier, J. M., Shakkottai, V., 2007. Modulators of small- and intermediate-conductance calcium-activated potassium channels and their therapeutic indications. Curr Med Chem 14, 1437-1457.

Wulff, H., Miller, M. J., Hansel, W., Grissmer, S., Cahalan, M. D., Chandy, K. G., 2000. Design of a potent and selective inhibitor of the intermediate-conductance Ca2+-activated K+ channel, IKCa1: a potential immunosuppressant. Proc Natl Acad Sci USA 97, 8151-8156.

Zhang, W., Ramamoorthy, Y., Kilicarslan, T., Nolte, H., Tyndale, R. F., Sellers, E. M., 2002. Inhibition of cytochromes P450 by antifungal imidazole derivatives. Drug Metab Dispos 30, 314-318.

Zuchero, J. B., Barres, B. A., 2015. Glia in mammalian development and disease. Development 142, 3805-3809.

The invention claimed is:

1. A method of treating ischemia/reperfusion brain injury, comprising the inhibition of calcium activated potassium channel $K_{Ca}3.1$ on microglia in the brain, by administering to a patient experiencing ischemia/reperfusion brain injury an amount of senicapoc sufficient to inhibit the calcium activated potassium channel $K_{Ca}3.1$ in brain microglia where the inhibition of microglia is sufficient to achieve a 50% inhibition in the release of nitric oxide from microglia in the brain when the senicapoc is administered to a patient.

2. A pharmaceutical composition for the treatment of ischemia/reperfusion brain injury comprising inhibiting a calcium activated potassium channel $K_{Ca}3.1$ on microglia in the brain, with a composition containing at least one excipient and an amount of senicapoc sufficient to inhibit the calcium activated potassium channel $K_{Ca}3.1$ in brain microglia where the inhibition of microglia is sufficient to achieve a 50% inhibition in the release of nitric oxide from microglia in the brain when the senicapoc is administered to a patient.

3. A method of treating ischemia/reperfusion brain injury, comprising the inhibition of calcium activated potassium channel $K_{Ca}3.1$ on microglia in the brain, by administering to a patient experiencing ischemia/reperfusion brain injury an amount of senicapoc sufficient to inhibit the calcium activated potassium channel $K_{Ca}3.1$ in brain microglia where the inhibition of microglia is sufficient to achieve a 50% inhibition in the release of interleukin 1β from microglia in the brain when the senicapoc is administered to a patient.

* * * * *